United States Patent [19]
Milstein

[11] Patent Number: 5,824,345
[45] Date of Patent: Oct. 20, 1998

[54] FRAGRANCES AND FLAVORANTS

[75] Inventor: Sam J. Milstein, Larchmont, N.Y.

[73] Assignee: Emisphere Technologies, Inc., Hawthorne, N.Y.

[21] Appl. No.: 484,293

[22] Filed: Jun. 7, 1995

[51] Int. Cl.$^6$ .............................. A61K 7/46; A61K 9/14; A61K 9/52; A61K 9/66

[52] U.S. Cl. ........................ 424/489; 424/401; 424/455; 264/4; 264/4.1; 514/772.3; 514/773; 514/783; 514/844; 514/951; 514/963

[58] Field of Search ..................................... 424/489, 401, 424/455; 514/772.3, 773, 783, 844, 951, 963; 264/4, 4.1

[56] References Cited

U.S. PATENT DOCUMENTS

| | | | |
|---|---|---|---|
| Re. 24,899 | 11/1960 | Green | 252/316 |
| 2,671,451 | 3/1954 | Bolger | 128/260 |
| 2,862,918 | 12/1958 | Meyer et al. | 260/123.5 |

(List continued on next page.)

FOREIGN PATENT DOCUMENTS

| | | | |
|---|---|---|---|
| 1077842 | 8/1976 | Canada | A61K 9/50 |
| 0 000 667 A1 | 2/1979 | European Pat. Off. | A61K 9/50 |
| 0 036 145 A1 | 9/1981 | European Pat. Off. | A61K 31/62 |
| 0 068 314 | 1/1983 | European Pat. Off. | . |
| 0 105 804 | 4/1984 | European Pat. Off. | C12N 15/00 |
| 0 130 162 A2 | 1/1985 | European Pat. Off. | B01J 13/02 |
| 0 170 540 A1 | 2/1986 | European Pat. Off. | A61K 9/52 |
| 0 342 054 A2 | 11/1989 | European Pat. Off. | A61K 7/06 |
| 0 342 056 A2 | 11/1989 | European Pat. Off. | A61K 7/06 |
| 0 365 183 | 4/1990 | European Pat. Off. | . |
| 0 366 277 | 5/1990 | European Pat. Off. | A61K 9/107 |
| 0 418 642 | 3/1991 | European Pat. Off. | . |
| 0 448 057 | 9/1991 | European Pat. Off. | C12P 21/08 |
| 0 459 795 | 12/1991 | European Pat. Off. | A61K 37/02 |
| 0 467 389 | 1/1992 | European Pat. Off. | A61K 9/52 |
| 0 490 549 A1 | 6/1992 | European Pat. Off. | A61K 47/12 |

(List continued on next page.)

OTHER PUBLICATIONS

Franssen et al., J. Med. Chem., 35:1246–1259, 1992.
Chemical Abstracts, 99(23):191473h, Dec. 5, 1983.
Kondo, *Microcapsule Processing and Technology*, pp. 154–165, 1979.
Pastores et al., *Journal of Liquid Chromatography*, 18:3049–3059, 1995.
Sinha et al., *Journal of Biological Chemistry*, 260:10714–10719, 1985.
Douglas et al., *Chemistry and Industry*, 22:748–751, 1985.
Finch, *Chemistry and Industry*, 22:752–756, 1985.
Chemical Abstracts, 76(14):72994u, (1971).
Chemical Abstracts, 84(7):44660d, (1975).
Chemical Abstracts, 86(16):107529g, (1976).
Chemical Abstracts, 112(15):134663h, (1989).
Chemical Abstracts, 114(22):214519x, (1990).
J. Györe et al., Thermal Analysis, vol. 2—Proceeding Fourth ICTA Budapest 1974, pp. 387–394.
Chemical Abstracts, 99(19) 158832b, (1982).
Derwent Abstracts, JP 67008622, (1967).

(List continued on next page.)

*Primary Examiner*—Thurman K. Page
*Assistant Examiner*—James M. Spear
*Attorney, Agent, or Firm*—Darby & Darby

[57] ABSTRACT

Compositions useful in the delivery of fragrances and flavorant active agents, and particularly vaporous fragrances and flavorants, are provided. These compositions include a microsphere which includes (a) the active agent; and (b) (i) a proteinoid, (ii) a modified hydrolyzed vegetable protein wherein the protein is modified with an amino reactive agent, or (iii) a combination thereof. Also contemplated is a method for preparing these compositions wherein the active agent is mixed with the proteinoid of hydrolyzed vegetable protein solution and the proteinoid or modified hydrolyzed vegetable protein is precipitated out of the solution, thereby forming a microsphere containing the active agent. In a further embodiment, the active agent is applied to a substrate.

22 Claims, 2 Drawing Sheets

Relative Concentration Of Clove Oil In Head Space

U.S. PATENT DOCUMENTS

| Patent No. | Date | Inventor | Class |
|---|---|---|---|
| 2,868,740 | 1/1959 | Luce | 260/8 |
| 2,971,916 | 2/1961 | Schleicher et al. | 252/62.5 |
| 3,016,308 | 1/1962 | Macaulay | 177/37 |
| 3,052,655 | 9/1962 | Fox et al. | 260/78 |
| 3,057,344 | 10/1962 | Abella et al. | 128/2 |
| 3,076,790 | 2/1963 | Fox et al. | 260/78 |
| 3,170,802 | 2/1965 | Fukushima | 99/145 |
| 3,190,837 | 6/1965 | Brynko et al. | 252/316 |
| 3,474,777 | 10/1969 | Figge et al. | 128/2 |
| 3,491,093 | 1/1970 | Pachter et al. | 260/247.5 |
| 3,565,559 | 2/1971 | Sato | 424/37 |
| 3,567,650 | 3/1971 | Bakan | 252/316 |
| 3,574,832 | 4/1971 | Engel et al. | 424/183 |
| 3,576,758 | 4/1971 | Emrick | 252/316 |
| 3,687,926 | 8/1972 | Arima et al. | 260/112.5 |
| 3,725,113 | 4/1973 | Chang | 117/82 |
| 3,748,277 | 7/1973 | Wagner | 252/316 |
| 3,794,561 | 2/1974 | Matsukawa et al. | 195/29 R |
| 3,795,739 | 3/1974 | Birkmayer et al. | 424/274 |
| 3,816,404 | 6/1974 | Kablaoui et al. | 260/239.3 A |
| 3,822,348 | 7/1974 | Higashi et al. | 424/95 |
| 3,849,550 | 11/1974 | Teitelbaum | 424/78 |
| 3,933,873 | 1/1976 | Love et al. | 260/404 |
| 3,937,668 | 2/1976 | Zolle | 252/316 |
| 3,939,253 | 2/1976 | Bodor et al. | 424/309 |
| 3,956,172 | 5/1976 | Saeki et al. | 252/316 |
| 3,962,416 | 6/1976 | Katzen | 424/19 |
| 3,976,773 | 8/1976 | Curran | 424/250 |
| 4,035,507 | 7/1977 | Bodor et al. | 424/311 |
| 4,048,268 | 9/1977 | Ludwig | 264/15 |
| 4,061,466 | 12/1977 | Sjoholm et al. | 23/230 B |
| 4,117,801 | 10/1978 | Dannelly et al. | 118/20 |
| 4,147,767 | 4/1979 | Yapel | 424/22 |
| 4,183,849 | 1/1980 | Hansen | 260/112.7 |
| 4,199,561 | 4/1980 | Roth et al. | 424/32 |
| 4,217,370 | 8/1980 | Rawlings et al. | 426/98 |
| 4,272,506 | 6/1981 | Schwarzberg | 424/8 |
| 4,289,759 | 9/1981 | Heavner et al. | 424/177 |
| 4,345,588 | 8/1982 | Widder et al. | 128/1.3 |
| 4,348,384 | 9/1982 | Horikoshi et al. | 424/101 |
| 4,351,337 | 9/1982 | Sidman | 128/260 |
| 4,352,883 | 10/1982 | Lim | 435/178 |
| 4,357,259 | 11/1982 | Senyei et al. | 252/316 |
| 4,388,304 | 6/1983 | Nyeki et al. | 424/177 |
| 4,402,856 | 9/1983 | Schnoring et al. | 428/402.22 |
| 4,405,598 | 9/1983 | Brown | 424/45 |
| 4,442,090 | 4/1984 | Kakeya et al. | 424/178 |
| 4,446,138 | 5/1984 | Pack | 424/248.57 |
| 4,450,150 | 5/1984 | Sidman | 424/1.1 |
| 4,460,563 | 7/1984 | Calanchi | 424/35 |
| 4,462,839 | 7/1984 | McGinley et al. | 106/198 |
| 4,462,991 | 7/1984 | Higuchi et al. | 424/177 |
| 4,473,620 | 9/1984 | Wu et al. | 428/402.24 |
| 4,483,807 | 11/1984 | Asano | 264/22 |
| 4,492,684 | 1/1985 | Goosen et al. | 424/19 |
| 4,518,433 | 5/1985 | McGinley et al. | 106/180 |
| 4,590,265 | 5/1986 | Bogan et al. | 536/63 |
| 4,608,278 | 8/1986 | Frank | 427/213.35 |
| 4,613,500 | 9/1986 | Suzuki et al. | 429/85 |
| 4,647,455 | 3/1987 | De Bold | 424/95 |
| 4,666,641 | 5/1987 | Fickat et al. | 264/4.3 |
| 4,671,954 | 6/1987 | Goldberg | 424/450 |
| 4,673,566 | 6/1987 | Goosen et al. | 424/19 |
| 4,703,042 | 10/1987 | Bodor | 514/56 |
| 4,708,952 | 11/1987 | Salatinjants | 514/158 |
| 4,745,161 | 5/1988 | Saudek et al. | 525/420 |
| 4,753,804 | 6/1988 | Iaccheri et al. | 424/491 |
| 4,757,007 | 7/1988 | Satoh | 435/69 |
| 4,757,024 | 7/1988 | Roper | 436/507 |
| 4,757,066 | 7/1988 | Shiokari et al. | 514/210 |
| 4,766,012 | 8/1988 | Valenti | 427/213.36 |
| 4,774,320 | 9/1988 | Tagliabue et al. | 530/328 |
| 4,789,734 | 12/1988 | Pierschbacher | 530/395 |
| 4,835,312 | 5/1989 | Itoh et al. | 564/205 |
| 4,837,381 | 6/1989 | Steber et al. | 424/502 |
| 4,844,904 | 7/1989 | Hamaguchi et al. | 424/450 |
| 4,873,087 | 10/1989 | Morishita et al. | 424/433 |
| 4,886,663 | 12/1989 | Houghten | 424/88 |
| 4,895,725 | 1/1990 | Kantor et al. | 424/455 |
| 4,897,444 | 1/1990 | Brynes et al. | 525/54.1 |
| 4,900,730 | 2/1990 | Miyauchi | 514/12 |
| 4,908,233 | 3/1990 | Takizawa et al. | 427/213.35 |
| 4,919,939 | 4/1990 | Baker | 424/493 |
| 4,925,673 | 5/1990 | Steiner | 424/455 |
| 4,963,364 | 10/1990 | Fox et al. | 424/455 |
| 4,976,968 | 12/1990 | Steiner | 424/491 |
| 4,983,402 | 1/1991 | Steiner | 424/491 |
| 4,996,292 | 2/1991 | Fox et al. | 528/328 |
| 5,039,481 | 8/1991 | Pacifici et al. | 422/4 |
| 5,055,300 | 10/1991 | Gupta | 424/409 |
| 5,066,487 | 11/1991 | Morelle et al. | 424/68 |
| 5,067,961 | 11/1991 | Kelman et al. | 623/5 |
| 5,069,936 | 12/1991 | Yen | 427/213.33 |
| 5,077,278 | 12/1991 | Hafner et al. | 514/30 |
| 5,100,669 | 3/1992 | Hyon et al. | 424/426 |
| 5,100,918 | 3/1992 | Sunshine et al. | 514/557 |
| 5,122,367 | 6/1992 | Ron et al. | 424/80 |
| 5,126,147 | 6/1992 | Silvestri et al. | 424/497 |
| 5,137,892 | 8/1992 | Chu et al. | 514/278 |
| 5,186,947 | 2/1993 | Goettsche et al. | 424/638 |
| 5,204,099 | 4/1993 | Barbier et al. | 424/401 |
| 5,206,384 | 4/1993 | Shibahara et al. | 548/537 |
| 5,216,124 | 6/1993 | Hansen, Jr. et al. | 530/317 |
| 5,244,653 | 9/1993 | Berke et al. | 424/70 |
| 5,250,236 | 10/1993 | Gasco | 264/4.4 |
| 5,271,961 | 12/1993 | Mathiowitz et al. | 427/213.31 |
| 5,278,148 | 1/1994 | Branca et al. | 514/19 |
| 5,328,992 | 7/1994 | Peter et al. | 534/116 |
| 5,352,461 | 10/1994 | Feldstein et al. | 424/493 |
| 5,384,133 | 1/1995 | Boyes et al. | 424/501 |
| 5,389,379 | 2/1995 | Dirix et al. | 424/451 |
| 5,418,010 | 5/1995 | Janda et al. | 427/213.31 |
| 5,439,686 | 8/1995 | Desai et al. | 424/451 |
| 5,536,813 | 7/1996 | Charpenel et al. | 530/324 |
| 5,705,529 | 1/1998 | Matyus et al. | 514/541 |

FOREIGN PATENT DOCUMENTS

| | | | |
|---|---|---|---|
| 0 517 211 A1 | 9/1992 | European Pat. Off. | A61K 47/12 |
| 0 616 799 A1 | 9/1994 | European Pat. Off. | A61K 7/00 |
| 2343037 | 3/1975 | Germany . | |
| 71258/2 | 12/1987 | Israel . | |
| 56-68612 | 6/1981 | Japan | A61K 31/19 |
| 58-35111 | 9/1983 | Japan | A61K 9/66 |
| 6-107682 | 4/1994 | Japan . | |
| 929401 | 6/1963 | United Kingdom . | |
| 1075952 | 8/1967 | United Kingdom . | |
| 1236885 | 6/1971 | United Kingdom . | |
| 1 567 763 | 5/1980 | United Kingdom | A61K 9/22 |
| 2 095 994 | 10/1982 | United Kingdom . | |
| WO 85/00105 | 1/1985 | WIPO | A61K 9/52 |
| WO85/00110 | 1/1985 | WIPO | A61K 47/00 |
| WO 85/02772 | 7/1985 | WIPO | A61K 49/00 |
| WO 87/04076 | 7/1987 | WIPO | A61K 45/02 |
| WO 88/01213 | 2/1988 | WIPO | B23B 5/16 |
| WO 92/19263 | 12/1992 | WIPO . | |
| WO 93/18754 | 9/1993 | WIPO | A61K 9/16 |
| WO 93/25583 | 12/1993 | WIPO | C07K 15/00 |
| WO 94/14420 | 7/1994 | WIPO | A61K 9/16 |
| WO 94/18950 | 9/1994 | WIPO | A61K 9/127 |
| WO 94/18997 | 9/1994 | WIPO | A61K 37/00 |
| WO 94/21234 | 9/1994 | WIPO | A61K 7/00 |
| WO 94/23702 | 10/1994 | WIPO | A61K 9/16 |

| | | | |
|---|---|---|---|
| WO 94/23767 | 10/1994 | WIPO | A61L 9/16 |
| WO 94/24291 | 10/1994 | WIPO | A61K 39/015 |
| WO 94/28878 | 12/1994 | WIPO | A61K 9/14 |
| WO 95/11690 | 5/1995 | WIPO | A61K 37/00 |

OTHER PUBLICATIONS

Airaudo, C.B. et al. (1987) *Journal of Food Service,* vol. 52(6), pp. 1750–1752.
Andini, S. et al. (1975) *Origins of Life,* vol. 6, pp. 147–153.
Brooke, S. 1 et al. (1977) *BioSystems,* vol. 9, pp. 1–22.
Chen et al. (1975) "Evidence for Hemiacetal Formation", *Biochemistry,* vol. 18, No. 5, pp. 921–925.
Davis et al. (1983) "Leucinal Inhibits . . . ", *Pharmacology Biochemistry Behavior,* vol. 19, pp. 791–794.
Dose, K. (1974) *Origins of Life,* vol. 5, pp. 239–252.
Fasman et al. (1964) *Biochemistry,* vol. 3, No. 11, pp. 1665–1674.
Fox, S.W. et al. (1976) *BioSystems,* vol. 8, pp. 40–44.
Fox, S.W. et al., *Molecular Evolution and the Origin of Life,* Maxel Decker, New York (1977).
Fox, S.W. et al. (1968) *Biochim. Biophys. Acta,* vol. 160, pp. 246–249.
Fox, S.W. (1976) *Origins of Life,* vol. 7, pp. 49–68.
Fox, S.W. (1980) *Naturwissenschaften,* vol. 67, pp. 378–383.
Fox, S.W. et al. (1960) *Archives of Biochemistry and Biophysics,* vol. 86, pp. 281–285.
Fox, S.W. et al. (1974) *Origins of Life,* vol. 5, pp. 227–237.
Fox, S.W. (1984) *Origins of Life,* vol. 14, pp. 485–488.
Gol'dovskii A.M. (1978) *Zhurnal Evolyutsionnoi Biokhimii i Fiziologii,* vol. 14(6), pp. 437–439.
Gurrieri, S. et al. (1973) *Thermochimica Acta,* vol. 7, pp. 231–239.
Harada, K. et al. (1979) *BioSystems,* vol. 11, pp. 47–53.
Harada et al., (1960) *Archives of Biochemistry and Biophysics,* vol. 86, pp. 274–280.
Heinrich, M.R. et al. (1969) *Archives of Biochemistry and Biophysics,* vol. 130, pp. 441–448.
Heinz, B. et al. (1981) *BioSystems,* vol. 14, pp. 33–40.
Hennon, G. et al. (1975) *Biochimie,* vol. 57, pp. 1395–1396.
Hsu, L.L. et al. (1976) *BioSystems,* vol. 8, pp. 89–101.
Hsu, L.L. et al. (1971) *Currents in Modern Biology,* vol. 4, pp. 12–25.
Ishima, Y. et al. (1981), *BioSystems,* vol. 14, pp. 243–251.
Jackson et al. (1991) "Pharmacological . . . ", *J. Pharm. & Exp. Thera.,* vol. 261, No. 1, pp. 546–552.
Jungck, J.R. et al. (1973) *Naturwissenschaften,* vol. 60, pp. 425–427.
Kokufuta, E. et al. (1984) *BioSystems,* vol. 16, pp. 175–181.
Lacey, Jr., J.C. et al. (1979) *BioSystems,* vol. 11, pp. 9–17.
Lacey, Jr., J.C. et al. (1979) *BioSystems,* vol. 11, pp. 1–7.
Martinez Luque–Romero, M. et al. (1986) *BioSystems,* vol. 19, pp. 267–272.
Masinovsky, Z. et al. (1989) *BioSystems,* vol. 22, pp. 305–310.
Matsuno, K. (1982) *BioSystems,* vol. 15, pp. 1–11.
Matsuno, K. (1984) *BioSystems,* vol. 17, pp. 11–14.
Matsuno, K. (1981) *BioSystems,* vol. 14, pp. 163–170.
McAlhaney, W.W. et al. (1976) *BioSystems,* vol. 8, pp. 45–50.
Melius, P. et al. (1987) *BioSystems,* vol. 20, pp. 213–217.
Melius, P. et al. (1975) *Bioorganic Chemistry,* vol. 4, pp. 385–391.
Melius, P. (1979) *BioSystems,* vol. 11, pp. 125–132.

Miquel, J. et al. (1971) *Currents in Modern Biology,* vol. 3, pp. 299–306.
Nakashima, T. et al. (1980) *J. Mol. Evol.,* vol. 15, pp. 161–168.
Nakashima, T. et al. (1981) *BioSystems,* vol. 14, pp. 151–161.
Novak, V.J.A. (1984) *Origins of Life,* vol. 14, pp. 513–522.
Olafsson, P.G. et al. (1971) *Polymer Letters,* vol. 9, pp. 521–528.
Phillips, R.D. et al. (1974) *Int. J. Peptide Protein Res.,* vol. 6, pp. 309–319.
Przybylski, A.T. et al. (1982) *Die Naturwissenschaften,* vol. 69, pp. 561–563.
Przybylski, A.T. et al. (1984) *Applied Biochemistry and Biotechnology,* vol. 10, pp. 301–307.
Przybylski, A.T. (1985) *BioSystems,* vol. 17, pp. 281–288.
Rohlfing, D.L. (1975) *Origins of Life,* vol. 6, pp. 203–209.
Rohlfing, D.L. (1970) *Science,* vol. 169, pp. 998–1000.
Rohlfing, D.L. (1967) *Archives of Biochemistry and Biophysics,* vol. 118, pp. 468–474.
Rohlfing, D.L. et al. *Catalytic Activities of Thermal Polyanhydro–α–Amino Acids,* pp. 373–418 (1975).
Rohlfing, D.L. et al. (1976) *BioSystems,* vol. 8, pp. 139–145.
Ryan, J.W. et al. (1973) *BioSystems,* vol. 5, pp. 115–118.
Saunders, M.A. et al. (1974) *BioSystems,* vol. 6, pp. 81–92.
Snyder, W.D. et al. (1975) *BioSystems,* vol. 7, pp. 222–229.
Sokol, P.E. (1974) *Journal of the American Oil Chemists'Society,* vol. 52, pp. 101–102.
Vaughan, G. et al. (1987) *BioSystems,* vol. 20, pp. 219–223.
Vol'kenshtein, M.V. (1989) *Molekulyarnaya Biologiya,* vol. 23(1), pp. 23–37.
Waehneldt, T.V. et al. (1968) *Biochim. Biophys. Acta,* vol. 160, pp. 239–245.
Williams et al. (1991) *J. Biol. Chem.,* vol. 266, No. 8, pp. 5182–5190.
Yuki, A. et al. (1969) *Biochemical and Biophysical Research Communications,* vol. 36(4), pp. 657–663.
Zulaski et al. (1983) "New Carboxyalkyl Inhibitors of Brain Enkenphalinase", *J. Med. Chem.,* 26, pp. 60–65.
(1985) *Chemical Abstracts,* vol. No. 105(1), Abstract No. 12027p.
(1985) *Chemical Abstracts,* vol. No. 102(6), Abstract No. 50870d.
Chemical Abstract, vol. 80(9) Abst. No. 52392a 1990.
Bergeron, Raymond J., et al. (1994) "Macromolecular Self–Assembly of Diketopiperazine Tetrapeptides", *Journal of the American Chemical Society,* vol. 116, pp. 8479–8484.
Bergeron, Raymond J., et al. (1993) "A Comparative Study of the Iron–Clearing Properties of Desferrithiocin Analogues With Desferrioxamine B in a Cebus Monkey Model", *Blood,* vol. 81, No. 8, pp. 2166–2173.
Bergeron, Raymond J., et al. (1992) "A Comparison of the Iron–Clearing Properties of 1,2–Dimethyl–3–Hydroxypyrid–4–One, 1,2–Diethyl–3–Hydroxypyrid–4–One, and Deferoxamine", *Blood,* vol. 79, No. 7, pp. 1882–1890.
Bergeron, Raymond J., et al. (1991) "Evaluation of Desferrithiocin and Its Synthetic Analogs as Orally Effective Iron Chelators", *Journal of Medicinal Chemistry,* vol. 34, No. 7, pp. 2072–2078.
Bergeron, Raymond et al., "A Comparative Evaluation of Iron Clearance Models", *Annals New York Academy of Sciences,* pp. 278–393 1990.
Andriuoli, G., et al. (1990), *Haemostasis* 20 (suppl. 1):154–158.

Caramazza, I., et al. (1991), *Thrombosis Research* 62:785–789.
Guarini, S., et al. (1983), *Experimentia* 41:350–352.
Guarini, S., et al. (1985), *Pharmacological Research Comunications* 17(8):685–697.
Dal Pozzo, A., et al. (1989), *Thrombosis Research* 56:119–124.
Gelb, R., et al (1983), *Lite Sciences* 33(1):83–85.
Watterberg et al. (1988), *Pediatric Research*, vol. 23, No. 4, part 2, p. 570A, col. 1, abstract no. 2209.
Bernstein (1985), *Chest* 87(1):68S–73S.
Damge et al. (1988), *Diabetes* 37:246–251.
*Chemical Abstracts*:83 184360k, (1975).
Amino, Y., et al., *Chem. Pharm. Bull.* 36(11):4426–4434 (1988).
Baughman, R.A. et al., *Proc. of the 6th Inter'l. Symp. on Recent Advs. in Drug Delivery Systems, Ctr. for Controlled Chem. Delivery, University of Utah*, Feb. 22–25, 1993, Salt Lake City, UT, pp. 179–180 "Method for Assessing The Stability of Proteinoid Microspheres".
Haas, S. et al., "Assessment Of Stability Of Proteinoid Microspheres", *Proceed. Intern. Symp. Control. Rel. Bioact. Mater.*, 20 (1993), Controlled Release Society, Inc.
X. Ma, et al., *Proceed. Intern. Symp. Control. Rel. Bioact. Mater.*, 20 (1993), Controlled Release Society, Inc. "In Vitro Mechanistic Investigation of the Proteinoid Microsphere Oral Delivery System".
Yen, H.–R H., et al., "Adsorption of Sulforhodamine 101 on Proteinoid Microspheres" *Proceed. Intern. Symp. Control. Rel. Bioact. Mater.*, 20 (1993), Controlled Release Society, Inc.
Presented at *"IBC Rational Drug Design Conference"*, San Diego, Calif.—Dec. 1994.
Bergeron, Raymond J. et al., *J. Am. Chem. Soc.* 1994, 116,8479–8484 "Macromolecular Self–Assembly of Diketopiperazine Tetrapeptides".
Leone–Bay et al., Presented at *"Winter Conference on Medicinal and Bioorganic Chemistry"* Steamboat Springs, Colorado—Feb. 1995 Microsphere Formation and Drug Delivery in a Series of Derivatized Amino Acids.
Santiago et al., *Pharm. Res.* 11: 1994, p. S–298 "Oral Delivery of Heparin Microspheres made with Modified Amino Acids".
Leone–Bay et al., *Pharm. Res.* 11: 1994, p. S–121 "Oral Delivery of Heparin using Acylated Amino Acids".
Sarubbi et al., *Pharm. Res.* 11: 1994, p. S–299 "Oral Calcitonin Delivery using the PODDS Technology".
Leipold et al., *Pharm. Res.* 11: 1994, p. S–298 "Oral Delivery of Interferon in Rats and Primates".
Santiago et al., *Pharm. Res.* 11: 1994, p. S–298 "Evaluation in Rats of Vehicles for the Oral Delivery of Low Molecular Weight Heparin".
X. Ma et al., PDD 7303 *Pharmaceutical Research* 9(10):S–244, 1992 (Oct. Supplement).
Milstein et al., *Symposia Abstracts*. AAPS Annual Meeting, San Antonia, TX, Nov. 15–19, 1993.

Santiago et al. "Initial Studies In The Assessment of Proteinoid Microsphere Activity" *Proceed. Intern. Symp. Control. Rel. Bioact. Mater.*, 20 (1993), Controlled Release Society, Inc.
Santiago et al. "Oral Immunization of Rats with Influenza Virus M Protein (M1) Microspheres" *Proceed. Intern. Symp. Control. Rel. Bioact. Mater.*, 19 (1992), Controlled Release Society, Inc., pp. 116–117.
Santiago et al. "Proteinoid Microspheres For The Oral Delivery of Heparin" *Proceed. Intern. Symp. Control. Rel. Bioact. Mater.*, 19 (1992), Controlled Release Society, Inc. pp. 514–515.
Santiago et al. *American Society for Microbiology* 92nd General Meeting, Abstract of the General Meeting, p. 159, May 26–30, 1992.
Milstein et al. "Preparation And In Vitro Characterization Of Proteinoid Microspheres" *Proceed Intern. Symp. Control. Rel. Bioact. Mater.*, 19 (1992), Controlled Release Society, Inc. pp. 516–517.
Doris K. Chiappetta, *Eastern Analytical Syposium*, Nov. 17, 1992 "Solutions for Problems in Bioanalysis".
Elizabeth A. Harris. M.S., *Eastern Analytical Symposium*, Nov. 17, 1992 "Solutions for Problems in Bioanalysis".
*AAPS 6TH Ann. Meeting and Expo.*, "Proteinoids—A Novel Drug Delivery System" Nov. 19, 1992, p. 33.
Milstein et al., "Efficient Oral Delivery Of Monoclonal Antibodies By Proteinoid Encapsulation" *The 1993 Miami Bio/Technology Winter Symposium—Advances in Gene Technology: Protein Engineering and Beyond*, Jan. 17–22, 1993.
Xinghang Ma, et al. "Stability Study of Drug–loaded Proteinoid Microsphere Formulations during Freeze–drying" *Journal of Drug Targeting*, 1994, vol. 2, pp. 9–21.
Baughman et al., "Screening Candidate Microsphere Formulations By Incubating In Simulated Digestive Fluids" *Proc. of the 6th Inter'l. Sympo. on Recent Advances in Drug Delivery Systems*, Ctr. for Controlled Chem. Delivery, University of Utah, Feb. 22–25, 1993, pp. 181–182.
Robert O. Dillman, M.D., Annals of Internal Medicine 1989:111 pp. 592–600, "Monoclonal Antibodies for Treating Cancer".
Brendan D. Curti, Critical Reviews in Oncology/Hematology, 1993: 14 pp. 29–39 "Physical barriers to drug delivery in tumors".
V. Hird et al, Genes and Cancer, edited by Desmond Carney & Karol Sikora, pp. 183–189, Immunotherapy with Monoclonal Antibodies. 1992.
Michael E. Osband et al., Immunology Today, vol. 11, No. 6 1990, pp. 93–95, "Problems in the investigational study and clinical use of cancer immunotherapy".
Tibtech Feb. 1993 vol. 11, pp. 42–44 "Therapeutic antibodies—the coming of age".
Thomas A. Waldmann, Articles Jun. 21, 1991, pp. 1657–1662, "Monoclonal Antibodies in Diagnosis and Therapy".

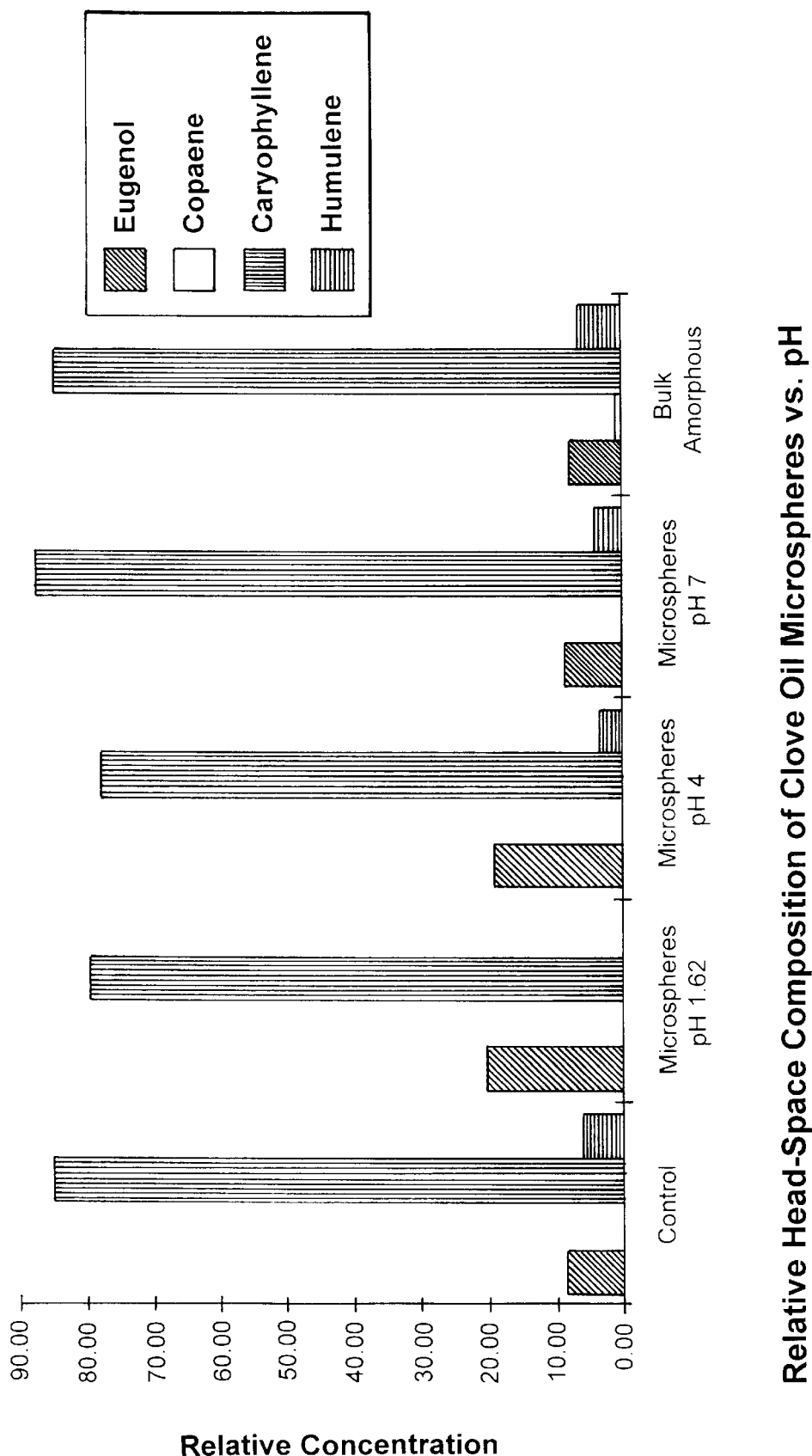

FRAGRANCES AND FLAVORANTS

FIELD OF THE INVENTION

The present invention relates to compositions which include fragrances or flavorants as active agents and to the delivery of such agents. These compositions are in the form of proteinoid or modified hydrolyzable vegetable protein microspheres which can be adapted to release the active agent in specific pH ranges. Methods for the preparation and for the use of such compositions are also disclosed.

BACKGROUND OF THE INVENTION

Proteinoid microspheres have been described for encapsulating pharmaceuticals for oral delivery (Steiner, et al., U.S. Pat. No. 4,925,673). However, it has now been discovered that other specific active agents can be delivered with proteinoid microspheres.

BRIEF DESCRIPTION OF THE DRAWINGS

FIG. 2 is a graphic illustration of the head space concentrations of the components of clove oil at various pH's from clove oil containing proteinoid microspheres in comparison with clove oil or clove oil in the presence of proteinoids that are not in microsphere form.

SUMMARY OF THE INVENTION

Figure 1:
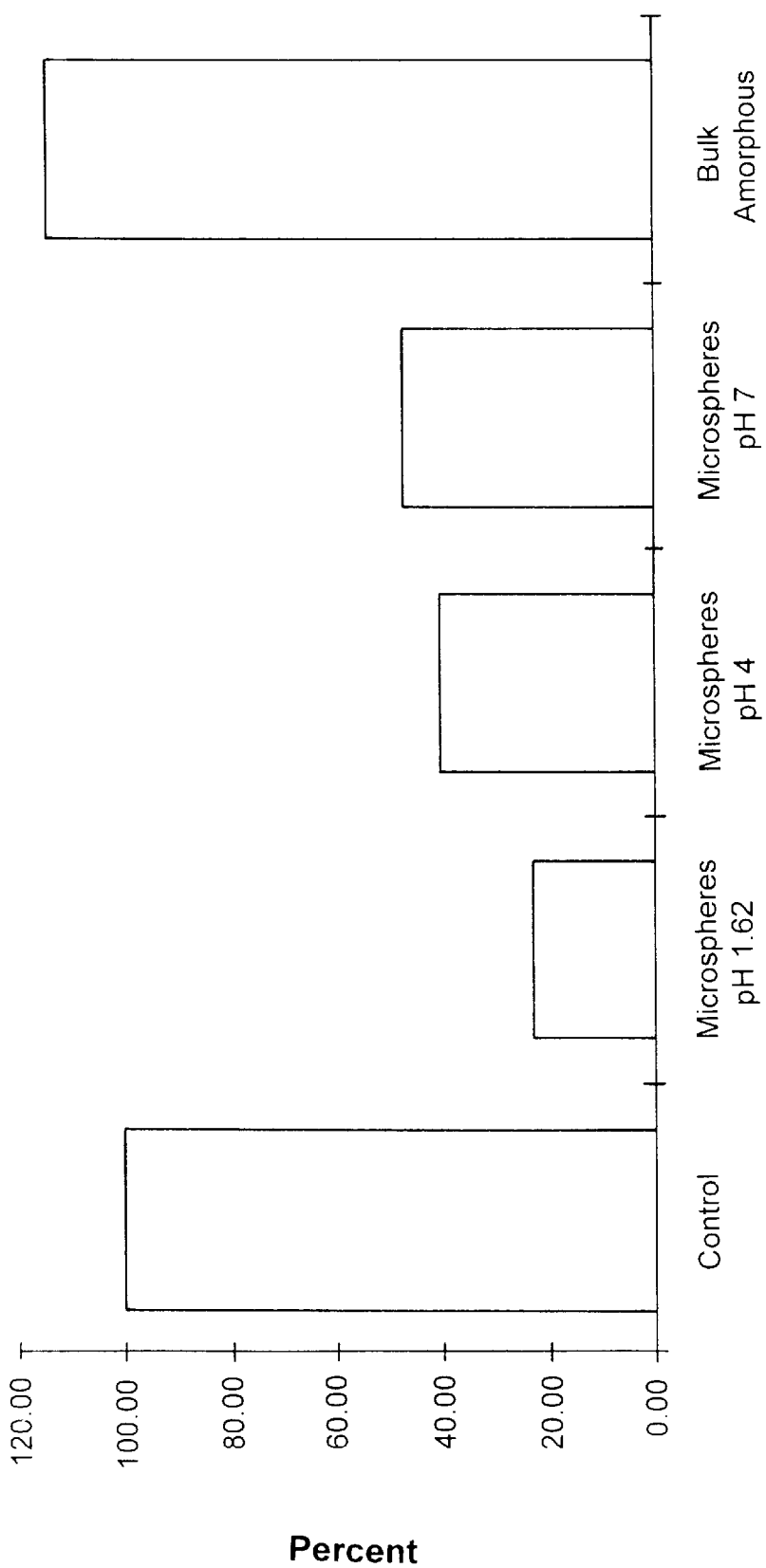
FIG. 1 is a graphic illustration of the head space concentrations of clove oil at various pH's from clove oil containing proteinoid microspheres in comparison with clove oil or clove oil in combination with proteinoids that are not in microsphere form.

Compositions useful in the delivery of fragrances and flavorant active agents, and particularly vaporous fragrances and flavorants, are provided. These compositions comprise a microsphere which comprises (a) the active agent; and (b) (i) a proteinoid, (ii) a modified hydrolyzed vegetable protein wherein the protein is modified with an amino reactive agent, or (iii) a combination thereof.

Also contemplated is a method for preparing these compositions wherein the active agent is mixed with the proteinoid of hydrolyzed vegetable protein solution and the proteinoid or modified hydrolyzed vegetable protein is precipitated out of the solution, thereby forming a microsphere containing the active agent.

In a further embodiment, the active agent is applied to a substrate.

DETAILED DESCRIPTION OF THE INVENTION

The present invention is suited to the delivery of active agents and fragrances or flavorants which optionally may be in a vaporous form either before or after incorporation into a microsphere. The present compositions incorporate readily available or easy to prepare, inexpensive starting materials. The formulation methods of the present invention are cost effective for preparing and isolating these compositions, are simple to perform, and are amenable to industrial scale for commercial production.

Active Agents

The active agents of the present invention include flavorants and fragrances. Flavorants are compounds or compositions that either increase or enhance an existing taste or that impart a specific taste. Fragrances are compounds or compositions that either increase or enhance an existing smell or odor or that impart a specific agreeable smell or odor. These fragrances and flavorants may be solids, liquids, vapors, or any combination thereof. Furthermore, they may completely or partially change state before being incorporated into a microsphere, while incorporated in a microsphere, or after being partially or completely released from a microsphere. Non-limiting examples of flavorants and fragrances are clove oil.

Vaporous active agents are those that are at least partially vaporous before incorporation in a microsphere and/or while incorporated in a microsphere.

The compositions of the present invention may include one or more active agents.

Proteinoids

Proteinoids are artificial polymers of amino acids. An amino acid is any carboxylic acid having at least one free amine group and includes naturally occurring and synthetic amino acids. Amino acids suitable for use herein include naturally occurring and synthetic amino acids as well as α- and non α-amino acids.

Representative, but not limiting, amino acids suitable for use in the present invention are generally of the formula

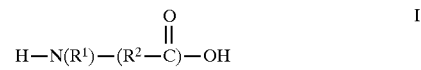

wherein:

$R^1$ is hydrogen, $C_1$–$C_4$ alkyl, or $C_2$–$C_4$ alkenyl;

$R^2$ is $C_1$–$C_{24}$ alkyl, $C_2$–$C_4$ alkenyl, $C_3$–$C_{10}$ cycloalkyl, $C_3$–$C_{10}$ cycloalkenyl, phenyl, naphthyl, ($C_1$–$C_{10}$ alkyl) phenyl, ($C_2$–$C_{10}$ alkenyl) phenyl, ($C_1$–$C_{10}$ alkyl) naphthyl, ($C_2$–$C_{10}$ alkenyl) naphthyl, phenyl ($C_1$–$C_{10}$ alkyl), phenyl ($C_2$–$C_{10}$ alkenyl), naphthyl ($C_1$–$C_{10}$ alkyl), or naphthyl ($C_2$–$C_{10}$ alkenyl);

$R^2$ being optionally substituted with $C_1$–$C_4$ alkyl, $C_2$–$C_4$ alkenyl, $C_1$–$C_4$ alkoxy, —OH, —SH, —$CO_2R^3$, $C_3$–$C_{10}$ cycloayl, $C_3$–$C_{10}$ cycloalkenyl, heterocycle having 3–10 ring atoms wherein the hetero atom is one or more of N, O, S, or any combination thereof, aryl, ($C_1$–$C_{10}$ alk)aryl, ar($C_1$–$C_{10}$ alkyl) or any combination thereof;

$R^2$ being optionally interrupted by oxygen, nitrogen, sulfur, or any combination thereof; and $R^3$ is hydrogen, $C_1$–$C_4$ alkyl, or $C_2$–$C_4$ alkenyl.

The preferred amino acids for use in the present invention are α-amino acids, and most preferably are naturally occurring α-amino acids. Many amino acids and amino acid esters are readily available from a number of commercial sources such as Aldrich Chemical Co. (Milwaukee, Wis., USA); Sigma Chemical Co. (St. Louis, Mo., USA); and Fluka Chemical Corp. (Ronkonkoma, N.Y., USA).

Preferred naturally occurring amino acids for use in the present invention as amino acids or components of a peptide are alanine, arginine, asparagine, aspartic acid, citrulline, cysteine, cystine, glutamine, glutamic acid, glycine, histidine, isoleucine, leucine, lysine, methionine, ornithine, phenylalanine, proline, serine, threonine, tryptophan, tyrosine, valine, hydroxy proline, γ-carboxyglutamate, phenylglycine, or O-phosphoserine. The preferred amino acids are arginine, leucine, lysine, phenylalanine, tyrosine, tryptophan, valine, and phenylglycine.

Non-limiting examples of non-naturally occurring amino acids for use in the present invention are β-alanine, α-amino butyric acid, γ-amino butyric acid, γ-(aminophenyl) butyric acid, α-amino isobutyric acid, citrulline, ε-amino caproic acid, 7-amino heptanoic acid, β-aspartic acid, aminobenzoic acid, aminophenyl acetic acid, aminophenyl butyric acid, γ-glutamic acid, cysteine, ε-lysine, methionine sulfone, norleucine, norvaline, ornithine, d-ornithine, p-nitrophenylalanine, hydroxy proline, 1,2,3,4,-tetrahydroisoquinoine-3-carboxylic acid, and thioproline.

The proteinoids useful herein preferably are prepared from mixed amino acids. Preferred proteinoids are condensation polymers, and most preferably, are thermal condensation polymers. These polymers may be directed or random polymers. Proteinoids can be linear, branched, or cyclical, and certain proteinoids can be units of other linear, branched, or cyclical proteinoids.

Special mention is made of diketopiperazines. Diketopiperazines are six member ring compounds. The ring includes two nitrogen atoms and is substituted at two carbons with two oxygen atoms. Preferably, the carbonyl groups are at the 1 and 4 ring positions. These rings can be optionally, and most often are, further substituted.

Diketopiperazine ring systems may be generated during thermal polymerization or condensation of amino acids or amino acid derivatives. (Gyore, J; Ecet M. *Proceedings Fourth ICTA (Thermal Analysis)*, 1974, 2, 387–394 (1974)). These six membered ring systems were presumably generated by intra-molecular cyclization of the dimer prior to further chain growth or directly from a linear peptide (Reddy, A. V., *Int. J. Peptide Protein Res.,* 40, 472–476 (1992); Mazurov, A. A. et al., *Int. J. Peptide Protein Res.,* 42, 14–19 (1993)).

Diketopiperazines can also be formed by cyclodimerization of amino acid ester derivatives as described by Katchalski et al., *J. Amer. Chem. Soc.,* 68, 879–880 (1946), by cyclization of dipeptide ester derivatives, or by thermal dehydration of amino acid derivatives and high boiling solvents as described by Kopple et al., *J. Org. Chem.,* 33 (2), 862–864 (1968).

Diketopiperazines typically are formed from α-amino acids. Preferably, the α-amino acids of which the diketopiperazines are derived are glutamic acid, aspartic acid, tyrosine, phenylalanine, and optical isomers of any of the foregoing.

Special mention is made of diketopiperazines of the formula

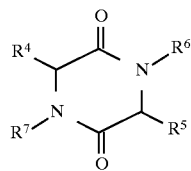

I wherein $R^4$, $R^5$, $R^6$, and $R^7$ independently are hydrogen, $C_1$–$C_{24}$ alkyl, $C_1$–$C_{24}$ alkenyl, phenyl, naphthyl, ($C_1$–$C_{10}$ alkyl)phenyl, ($C_1$–$C_{10}$ alkenyl)phenyl, ($C_1$–$C_{10}$ alkyl)naphthyl, ($C_1$–$C_{10}$ alkenyl)naphthyl, phenyl ($C_1$–$C_{10}$ alkyl), phenyl($C_1$–$C_{10}$ alkenyl), naphthyl ($C_1$–$C_{10}$ alkyl), and naphthyl ($C_1$–$C_{10}$ alkenyl); any of $R^4$, $R^5$, $R^6$, and $R^7$ independently may optionally be substituted with $C_1$–$C_4$ alkyl, $C_1$–$C_4$ alkenyl, $C_1$–$C_4$ alkoxy, —OH, —SH, and —$CO_2R^8$ or any combination thereof; $R^8$ is hydrogen, $C_1$–$C_4$ alkyl or $C_1$–$C_4$ alkenyl; and any of $R^4$, $R^5$, $R^6$, and $R^7$ independently may optionally be interrupted by oxygen, nitrogen, sulfur, or any combination thereof.

The phenyl or naphthyl groups may optionally be substituted. Suitable, but non-limiting, examples of substituents are $C_1$–$C_6$ alkyl, $C_1$–$C_6$ alkenyl, $C_1$–$C_6$ alkoxy, —OH, —SH, or $CO_2R^9$ wherein $R^9$ is hydrogen, $C_1$–$C_6$ alkyl, or $C_1$–$C_6$ alkenyl.

Preferably, $R^6$ and $R^7$ independently are hydrogen, $C_1$–$C_4$ alkyl or $C_1$–$C_4$ alkenyl. Special mention is made of diketopiperazines which are preferred complexing perturbants. These diketopiperazines include the unsubstituted diketopiperazine in which $R^4$, $R^5$, $R^6$, and $R^7$ are hydrogen, and diketopiperazines which are substituted at one or both of the nitrogen atoms in the ring, i.e. mono or di-N-substituted. Special mention is made of the N-substituted diketopiperazine wherein one or both of the nitrogen atoms is substituted with a methyl group.

Special mention is also made of diketopiperazines of the formula

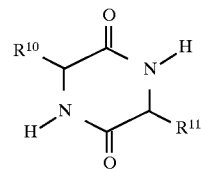

II wherein $R^{10}$ and $R^{11}$ independently are hydrogen, $C_1$–$C_{24}$ alkyl, $C_1$–$C_{24}$ alkenyl, phenyl, naphthyl, ($C_1$–$C_{10}$ alkyl) phenyl, ($C_1$–$C_{10}$ alkenyl)phenyl, ($C_1$–$C_{10}$ alkyl)naphthyl, ($C_1$–$C_{10}$ alkenyl)naphthyl, phenyl ($C_1$–$C_{10}$ alkyl), phenyl ($C_1$–$C_{10}$ alkenyl), naphthyl ($C_1$–$C_{10}$ alkyl), and naphthyl ($C_1$–$C_{10}$ alkenyl); but both $R^{10}$ and $R^{11}$ can not be hydrogen; either or both $R^{10}$ or $R^{11}$ independently may optionally be substituted with $C_1$–$C_4$ alkyl, $C_1$–$C_4$ alkenyl, $C_1$–$C_4$ alkoxy, —OH, —SH, and —$CO_2R^{12}$ or any combination thereof; $R^{12}$ is hydrogen, $C_1$–$C_4$ alkyl or $C_1$–$C_4$ alkenyl; and either or both $R^{10}$ and $R^{11}$ independently may optionally be interrupted by oxygen, nitrogen, sulfur, or any combination thereof.

The phenyl or naphthyl groups may optionally be substituted. Suitable, but non-limiting, examples of substituents are $C_1$–$C_6$ alkyl, $C_1$–$C_6$ alkenyl, $C_1$–$C_6$ alkoxy, —OH, —SH, or $CO_2R^{13}$ wherein $R^{13}$ is hydrogen, $C_1$–$C_6$ alkyl, or $C_1$–$C_6$ alkenyl. When one of $R^{10}$ or $R^{11}$ is hydrogen, the diketopiperazine is mono-carbon-(C)-substituted. When neither $R^{10}$ nor $R^{11}$ is hydrogen, the diketopiperazine is di-carbon-(C)-substituted.

Preferably, $R^{10}$, $R^{11}$, or both $R^{10}$ and $R^{11}$, contain at least one functional group, a functional group being a non-hydrocarbon portion responsible for characteristic reactions of the molecule. Simple functional groups are heteroatoms including, but not limited to halogens, oxygen, sulfur, nitrogen, and the like, attached to, the carbon of an alkyl group by a single or multiple bond. Other functional groups include, but are not limited to, for example, hydroxyl groups, carboxyl groups, amide groups, amine groups, substituted amine groups, and the like.

Preferred diketopiperazines are those which are substituted at one or two of the carbons of the ring with a functional group that includes at least one carboxyl functionality.

Modified Hydrolyzed Vegetable Protein

Modified hydrolyzed vegetable protein is prepared from hydrolyzed vegetable protein. Hydrolyzed vegetable protein is a product which is derived from defatted vegetable meal. In practicing the present invention, acid or enzyme hydrolyzed vegetable proteins are useful. The vegetable proteins generally contain titratable carboxylic acid groups (COOH) ranging from about 3 to about 8 milliequivalents/g, preferably from about 4 to about 6 milliequivalents/g, and total free amino groups ($NH_2$) ranging from about 3 to about 9 milliequivalents/g, preferably ranging from about 4 to about 7 milliequivalents/g $NH_2$. The molecular weight of the hydrolyzed vegetable protein ranges from about 100 daltons to about 2000 Daltons, and preferably from about 200 to about 500 daltons.

Hydrolyzed vegetable protein is available from a variety of commercial sources, such as, for example, Ajinomoto USA, Inc. (Teaneck, N.J.); Central Soya Co., Inc. (Fort Wayne, Ind.); Champlain Industries, Inc. (Clifton, N.J.); Archer Daniels Midland (Decatur, Ill.), A. E. Staley Company, Gunther Products Division, (Decatur, Ill.), and additional companies listed in "Food Engineering Master", an annual publication of Chilton Co., Radnor, Pa. A preferred hydrolyzed vegetable protein in practicing this invention is available from Ajinomoto USA under the tradename AJI-EKI. This product is an acid hydrolyzed liquid soybean protein which is derived from defatted soybean meal. Other preferred hydrolyzed soy proteins include PROFAM 781, available from Archer Daniels Midland and PTOT 1550 and MIR-A-FOAM 100 available from A. E. Staley, Gunther Products division.

If desired, a dried protein extract of the hydrolyzed vegetable protein solution may be used to prepare the modified hydrolyzed vegetable protein of the invention. The dried protein extract is preparable by extracting the hydrolyzed vegetable protein solution with a suitable solvent, e.g., methanol, followed by evaporating the solvent extract.

The hydrolyzed vegetable protein is modified by an amine reactive agent. Typically the hydrolyzed vegetable protein is modified by acylating or sulfonating at least one free amine group, with an acylating or sulfonating agent which reacts with at least one of the free amine groups present. Suitable, but non-limiting, examples of acylating or sulfonating agents useful for preparing the modified hydrolyzed vegetable protein emulsifiers of the present invention include acylating and sulfonating agents having the formula:

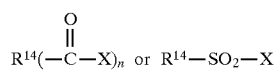

wherein $R^{14}$ is alkyl or alkenyl, preferably having from 1 to 20 carbon atoms, or aromatic preferably having from 6 to 20 carbon atoms and n is 1 or 2.

The $R^{14}$ group can be substituted or unsubstituted, The preferred substituents include $C_1$ to $C_4$ alkyl, $C_1$ to $C_4$ alkenyl, $C_1$ to $C_4$ alkoxy, $CO_2R^{15}$ wherein $R^{15}$ is hydrogen, $C_1$ to $C_4$ alkyl or $C_1$ to $C_4$ alkenyl.

Preferably, $R^{14}$ is methyl, ethyl, phenyl, benzyl or naphthyl. More preferably, $R^{14}$ is phenyl, or acetyl. X is a leaving group. In a reaction in which the substrate molecule becomes cleaved, part of it (the part not containing the carbon) is usually called the leaving group. See *Advanced Organic Chemistry*, 2d edition, Jerry March, New York: McGraw-Hill Book (1977), page 187, Typical leaving groups include, but are not limited to, halogens such as chlorine, bromine and iodine.

Examples of the acylating and sulfonating agents for modifying hydrolyzed vegetable protein include, but are not limited to, acyl halides, such as, for example, acetyl chloride, propyl chloride, benzoyl chloride, phthaloyl chloride, hexahydrophthaloyl chloride, tetrahydrophthaloyl chloride, cyclohexanoyl chloride, sebacoyl chloride, hippuryl chloride and the like; sulfonyl halides, such as, for example, benzene sulfonyl chloride, acetylsulfanilyl chloride, and the like; anhydrides, such as, for example, acetic anhydride, propyl anhydride, benzoic anhydride, maleic anhydride, phthalic anhydride, tetrahydrophthalic anhydride, hexahydrophthalic anhydride, hippuric anhydride and the like. The preferred acylating and sulfonating agents are benzoyl chloride, benzene sulfonyl chloride, cyclohexanoyl chloride, phthalic anhydride, tetrahydrophthalic anhydride, and hexahydrophthalic anhydride.

The hydrolyzed vegetable protein is typically modified by first dissolving it in aqueous alkaline solution of a metal hydroxide, e.g., sodium or potassium hydroxide, and heating at the solution to a temperature ranging from about 50° C. to about 70° C., preferably from about 50° C. to about 60° C., for a period ranging from about 10 minutes to about 40 minutes, preferably about 15 minutes. The amount of alkali employed per mmole of titratable $NH_2$ in the hydrolyzed vegetable protein generally ranges from about 2 to about 3 mmole, and preferably from about 2.2 to about 2.5 mmole. The pH of the solution is generally maintained from about 8 to about 13, preferably ranging from about 9 to about 10.

Thereafter, the acylating or sulfonating agent is added to the reaction mixture. The amount of acylating or sulfonating agent in relation to the quantity of hydrolyzed vegetable protein employed is based on the equivalents of total free $NH_2$ in the hydrolyzed vegetable protein. Thus, from about 0.3 to about 1.2 equivalents of acylating or sulfonating agent are used for each molar equivalent of total $NH_2$ groups in the hydrolyzed vegetable protein, and preferably from about 0.6 to about 1.0 equivalent of acylating or sulfonating agent for each molar equivalent of groups $NH_2$ groups in the hydrolyzed vegetable protein. The modified hydrolyzed vegetable protein is then recovered from the reaction mixture using standard techniques, such as, for example, precipitation with dilute acid and filtration of the precipitate. See also, PCT Publication No. WO94/14420 (Jul. 7, 1994).

Microspheres

The microspheres of the present invention can generally be of a matrix form or the microcapsule form. The matrix form includes both hollow matrix spheres in which the proteinoid forms a matrix shell around a hollow center, and the active agent is distributed throughout the matrix, and a solid matrix sphere in which the proteinoid forms a circle matrix continuing in which the active agent is distributed. The microcapsule form is one in which the encapsulated active agent either is in a vapor solution, a solid state, or any combination thereof, with the carrier forming a shell around the encapsulated material. The microcapsule form is the form most often taken by the self assembly with the proteinoids of the present invention. The microspheres can also have the flavor or fragrance adsorbed thereon. The microspheres are preferably non-porous.

Microspheres can be prepared by dissolving the carrier, i.e., proteinoid or modified hydrolyzed vegetable protein in an appropriate solvent and then stimulating self assembly by contacting the carrier solution with a precipitator. Solubility of the carrier can be regulated by the selection of the appropriate amino acid.

Furthermore, the carrier, and therefore, the microsphere compositions of the present invention can be pH adapted to be selectively soluble in specific acidic, basic, or neutral pH ranges.

Compositions which are targeted to an acidic environment can be made selectively soluble at specific ranges of acidic pH. These compositions are prepared with an acid-soluble carrier. The acid-soluble carrier exists largely in the cation form in at least a portion of the pH range from about 1 to about 6.8. However, outside the selected range, such as for example, at a different acidic pH or above about 6.8 or at selected ranges above pH 6.8, the carrier is largely unprotonated and insoluble in water. Therefore, the carrier could self assemble to microspheres at a different acidic pH or at a basic or neutral pH, and the active agent in the composition would not be released until the carrier solubilizes upon encountering the selected acidic pH.

Compositions which are to be targeted to an alkaline environment can be made selectively soluble at specific ranges of alkaline pH. These compositions are prepared with a base-soluble carrier. The base-soluble carrier exists largely in an anionic form in at least a portion of the pH range of from about 7.2 to about 11. However, outside the selected range, such as for example, a different basic pH or below and at pH 7.2, the carrier is largely protonated and insoluble in water. Therefore, the carrier could self assemble to microspheres at a different basic pH or acidic or neutral pH, and the active agent in the composition would not be released until the carrier solubilizes upon encountering the selected basic pH.

Compositions which are targeted to a neutral environment can be made selectively soluble at neutral pH. These compositions are prepared with a neutral-soluble carrier. The neutral-soluble carrier exists largely in a neutral form at neutral pH, i,e. from about 6.8 to about 7.2. However, above or below this range, the carrier is insoluble in water. Therefore, the carrier could self assemble to microspheres at acidic or basic pH, and the active agent in the composition would not be released until the carrier solubilizes upon encountering a neutral pH.

In a typical formulation, the final solution can contain from about 10 mg to about 2000 mg of carrier per ml of solution, preferably between about 75 to about 500 mg of carrier per ml of solution, and most preferably from about 75 to about 200 mg per ml. Optionally, the mixture is heated to a temperature between about 20° C. and about 60° C., preferably about 40° C., until the carrier dissolves. Particulates remaining in the solution may be filtered out by conventional means such as gravity filtration over filter paper. The carrier solution usually is maintained at the elevated temperature and is mixed with the non-biologically active agent and a precipitator, for example, an acid solution such as, for example, aqueous acetic or citric acid at a concentration ranging from about 1N to about 3N for acid insoluble carriers, a basic solution for base insoluble carriers, and a neutralizing solution for neutral insoluble carriers. The active agent can be mixed with the precipitating solution or can be used separately. The resultant mixture is maintained for a period of time sufficient for microsphere formation as observed by light microscopy. Although it is preferred that the precipitating solution is added to the carrier solution, the carrier solution can be added to the precipitating solution as well.

The solutions above may optionally contain additives such as stabilizing additives. The presence of such additives promotes the stability and dispersability of the non-biologically active agent in solution. The stabilizing additives may be employed at a concentration ranging between about 0.1 and 5% (w/v), preferably about 0.5% (w/v). Suitable, but non-limiting examples of stabilizing additives include buffer salts, gum acacia, gelatin, methyl cellulose, polyethylene glycol, and polylysine. The preferred stabilizing agents are gum acacia, gelatin, and methyl cellulose.

The amount of active agent that may be encapsulated by the microsphere is dependent upon a number of factors which include the concentration of active agent in the microsphere or precipitator solution as well as the affinity of the active agent for the proteinoid. The concentration of the active agent in the final formulation also will vary depending on the required amount for treatment. When necessary, the exact concentration can be determined by, for example, reverse phase HPLC analysis.

When the present compositions are in microsphere form, the particle size of the microsphere can also aid in providing efficient delivery of the active agent. Typically, microspheres of the present invention will have a diameter of less than 10 $\mu$m, preferably in the range of from about 0.1 $\mu$m to about 10 $\mu$m, and most preferably in the range of from 0.2 $\mu$m to about 10 $\mu$m. The size of the microspheres containing an active agent can be controlled by manipulating a variety of physical or chemical parameters, such as the pH, osmolarity, ionic strength of the encapsulating solution, or size of the ions in solution, and/or by the choice of the precipitator used in the microsphere forming and loading process.

The compositions of the present invention may be formulated into unit forms by the addition of one or more excipient(s), diluent(s), disintegrant(s), lubricant(s), plasticizer(s), colorant(s), or carrier vehicle(s). Preferred unit forms are liquids or aerosols.

The compositions will include activity effective amounts of the active agent or can include less than such an amount if multiple applications are to be used to deliver or apply a total activity effective amount of the active agent. Unit forms are prepared by methods conventional in the art.

The compositions of the subject invention are useful for applying non-biologically active agents to any substrates such as for example, skin, air, fixtures, carpets, hard or soft surfaces, water systems, etc., particularly in those in which pH changes. The compositions are applied by, for example, contacting the composition with the substrate.

DESCRIPTION OF THE PREFERRED EMBODIMENTS

The following examples illustrate the invention without limitation. All parts are given by weight unless otherwise indicated.

Example 1

Clove Oil/Proteinoid Microspheres

Clove oil/proteinoid microspheres were prepared by combining a mixture of 0.1% clove oil in 10% soluble proteinoid (Glu-Asp-Tyr-Phe) with an equal volume of 1.7N citric acid and gum to prepare a microsphere of clove oil/proteinoid microsphere.

Clove oil is a relatively simple mixture of products obtained from the extraction of clove. The major components in the extract are a mixture of eugenol, caryophyllene, eugenol acetate, humulene, and copaene. Their structures are shown below.

Eugenol trans-Caryophyllene

-continued

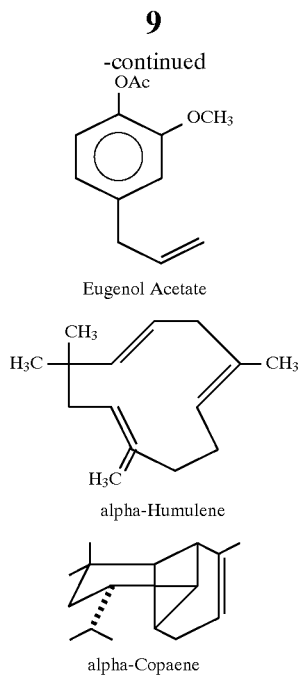

Eugenol Acetate alpha-Humulene alpha-Copaene

A 0.05% clove oil in 0.85N citric acid and gum mixture was prepared as a control, and 1 mL was transferred to a separate head-space vial. An additional sample was prepared by transferring the bulk amorphous material obtained from the preparation of the proteinoid to a vial containing 1 mL of 0.85N citric acid and gum.

Each vial was individually heated for 5 minutes at 80° C., and then was pressurized to 300 psi for 3 minutes with helium. The head-space of each vial was equilibrated in a 250 μL injection loop and then transferred to an HP 5890 gc equipped with an HP 5971 MSD. The components in the vial head-space were chromatographed on an HP cross-linked 5% methylphenyl silicon column. The composition of the separate peaks in the chromatograms were identified by comparing their mass spectrum with the mass spectrum of authentic samples from a Wiley database.

The following parameters were used to acquire the chromatograms: injector port temperature=250° C., Oven temperature=100° C. for 2 minutes, then 10° C./min to 150° C. for 10 minutes, detector transfer line temperature=180° C.

Results are summarized in Tables 2 and 3 below and are illustrated in FIGS. 1 and 2.

TABLE 2

Peak Areas of the Components in the Head-space of Clove Oil Proteinoid

| *Sample | Eugenol | Copaene | Caryophyllene | Humulene | Total Area | Relative Area |
|---|---|---|---|---|---|---|
| Control | 1657743 | trace | 16244172 | 1188710 | 19090625 | 100.00 |
| Microspheres pH 1.62 | 892886 | trace | 3495762 | trace | 4388648 | 22.99 |
| Microspheres pH 4 | 1466342 | trace | 6042377 | 253367 | 7762086 | 40.66 |
| Microspheres pH 7 | 7654119 | trace | 7906257 | 365303 | 9036979 | 47.34 |
| Bulk Amorphous | 1730197 | 223071 | 18489962 | 1421563 | 21864793 | 114.53 |

The percentages of each component of the oil are summarized in Table 1.

TABLE 1

Relative Composition of Clove Oil Determined by Gas Chromatography-Mass Spectrometry Percentage of the Total Composition

| Method of Analysis | Eugenol | Eugenol Acetate | trans-Caryophyllene | alpha-Humulene |
|---|---|---|---|---|
| Direct Injection | 88.5 | 3.2 | 7.4 | 0.8 |
| Head-Space* | 6.9 | trace | 78.0 | 7.5 |
| Head-Space** | 27.8 | — | 52.6 | 4.2 |

*3.8% copaene is present (sample preparation: 1μ liter clove oil in 1.7 grams of DI H$_2$O
**7.8% copaene is present (sample preparation: 1μ liter clove oil neat)

The final concentration of eugenol in the suspension was 0.05%, which is the saturated solubility of clove oil in deionized water. The pH of the suspension was 1.62.

A 1 mL aliquot of the suspension was transferred to three separate 20 mL crimp-top vials. Two of the three vials were adjusted to pH 4 and 7, respectively, by addition of several drops of aqueous NaOH. All the vials were then sealed and placed in a Tekmar 7000 head-space autosampler.

TABLE 3

Relative Composition of the Head-Space from Clove-Oil Microspheres vs. pH

| | | Relative Peak Area | | | Total Peak Area |
|---|---|---|---|---|---|
| Sample | Eugenol | Copaene | Caryophyllene | Humulene | |
| Control | 8.68 | 0.00 | 85.09 | 6.23 | 100 |
| Microspheres pH 1.62 | 20.35 | 0.00 | 79.65 | 0.00 | 100 |
| Microspheres pH 4 | 18.89 | 0.00 | 77.84 | 3.26 | 100 |
| Microspheres pH 7 | 8.47 | 0.00 | 87.49 | 4.04 | 100 |
| Bulk Amorphous | 7.91 | 1.02 | 84.56 | 6.50 | 100 |

Results and Discussion

Table 2 and FIG. 1 illustrate that the clove oil/microspheres (pH=1.62) contained approximately 23% of the amount of clove oil otherwise present in the control sample. When, the pH of the clove/oil microsphere sample was increased to 4, the relative concentration of clove oil in the microspheres increased to 41%. A similar increase in clove oil concentration was observed when the pH of the clove/oil microspheres sample was adjusted to 7.

The results indicate that the eugenol/microspheres behave as a pH-mediated delivery system for eugenol. When the pH is increased, microspheres dissolve and release the clove oil components. The data in Table 2 shows the bulk amorphous material contained most of the clove oil used to prepare the microspheres. This may be expected since the amorphous material probably represents the majority of the proteinoid used in the preparation of the proteinoid microspheres.

Table 3 and FIG. 2 illustrate that the relative composition of the head-space from the bulk amorphous sample closely parallels that from the control, but that there are subtle variations in the relative composition of the head-space of the clove/oil microspheres with increasing pH. As the pH of the microsphere suspension increases, the concentration of eugenol relative to the total clove-oil composition decreases. This suggests that the eugenol may be free or weakly bound to the microspheres. In contrast, the hydrophobic components in the clove oil. i.e. caryophyllene, humulene, and copaene, are released from the microspheres upon dissolution. Therefore, eugenol makes a smaller contribution to the total head-space composition of the clove-oil microspheres.

Example 2

Clove Oil/Modified Hydrolyzed Vegetable Protein

The method of Example 1 is followed substituting modified hydrolyzed soybean protein for the proteinoid.

All applications, patents, test methods, and publications mentioned are herein are hereby incorporated by reference. Many variations of the present invention will suggest themselves to those skilled in the art in light of the above detailed disclosure. All such modifications are within full intended scope of the appended claims.

I claim:

1. A composition comprising a microsphere, said microsphere comprising:
   (a) an active agent comprising a member selected from the group consisting of a perfume, a vapor, or a combination thereof, and
   (b) (i) a proteinoid, (ii) a modified hydrolyzed vegetable protein wherein said protein is modified with an amine reactive agent, or (iii) a combination thereof;
   wherein said microsphere can release the active agent.

2. A composition as defined in claim 1, wherein said active agent comprises a perfume.

3. A method for applying an active agent to a substrate, said method comprising contacting said substrate with a composition as defined in claim 1.

4. A composition as defined in claim 1, wherein said active agent comprises a vapor.

5. A composition as defined in claim 1, wherein said proteinoid comprises mixed amino acids.

6. A composition as defined in claim 5, wherein said proteinoid comprises a polymer of mixed amino acids.

7. A composition as defined in claim 1, wherein said proteinoid comprises a condensation polymer.

8. A composition as defined in claim 7, wherein said proteinoid comprises a thermal condensation polymer.

9. A composition as defined in claim 1, wherein said proteinoid comprises a directed polymer.

10. A composition as defined in claim 1, wherein said proteinoid comprises a random polymer.

11. A composition comprising a microsphere, said microsphere comprising:
    (a) an active agent comprising a member selected from the group consisting of a perfume, a vapor, and a combination thereof, and
    (b) (i) a proteinoid comprising a diketopiperazine, (ii) a modified hydrolyzed vegetable protein wherein said protein is modified with an amine reactive agent, or (iii) a combination thereof:
    wherein said microsphere can release the active agent.

12. A composition comprising a microsphere, said microsphere comprising:
    (a) an active agent comprising a member selected from the group consisting of a perfume, a vapor, and a combination thereof, and
    (i) a proteinoid, (ii) a modified hydrolyzed vegetable protein comprising acid hydrolyzed soybean protein, wherein said protein is modified with an amine reactive agent, or (iii) a combination thereof:
    wherein said microsphere can release the active agent.

13. A composition as defined in claim 1, wherein said amine reactive modifying group is selected from the group consisting of a benzene sulfonyl group, a benzoyl group, a phthaloyl group, a tetrahydrophthaloyl group, and a cyclohexanoyl group.

14. A composition as defined in claim 1, wherein said microsphere comprises a microcapsule.

15. A composition as defined in claim 14, wherein said microcapsule is non-porous.

16. A method as defined in claim 3, wherein said substrate comprises skin.

17. A composition as defined in claim 16, wherein said composition is adapted to release said active agent at an acidic pH.

18. A composition as defined in claim 16, wherein said composition is adapted to release said active agent at an basic pH.

19. A composition as defined in claim 16, wherein said composition is adapted to release said active agent at a neutral pH.

20. A composition as defined in claim 1, wherein said microsphere has a diameter less than of 10 µm.

21. A composition comprising:
    (a) a vaporous active agent, in
    (b) a microsphere comprising a proteinoid, a modified hydrolyzed vegetable protein wherein said protein is modified with an amine reactive agent, or a combination thereof;
    wherein said microsphere can release the active agent.

22. A method for preparing a composition as defined in claim 1.

* * * * *